(12) United States Patent
Ferree et al.

(10) Patent No.: US 8,784,492 B2
(45) Date of Patent: *Jul. 22, 2014

(54) ARTIFICIAL DISC REPLACEMENTS WITH NATURAL KINEMATICS

(71) Applicant: SpineCore, Inc., Allendale, NJ (US)

(72) Inventors: Bret A. Ferree, Cincinnati, OH (US); David Tompkins, Milford, OH (US)

(73) Assignee: SpineCore, Inc., Allendale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/737,500

(22) Filed: Jan. 9, 2013

(65) Prior Publication Data

US 2013/0131813 A1 May 23, 2013

Related U.S. Application Data

(63) Continuation of application No. 10/512,515, filed as application No. PCT/US03/12500 on Apr. 23, 2003, now Pat. No. 8,366,772, which is a continuation of application No. 10/420,423, filed on Apr. 22, 2003, now Pat. No. 6,706,068.

(60) Provisional application No. 60/374,747, filed on Apr. 23, 2002, provisional application No. 60/445,958, filed on Feb. 7, 2003, provisional application No. 60/449,642, filed on Feb. 24, 2003.

(51) Int. Cl.
*A61F 2/44* (2006.01)

(52) U.S. Cl.
USPC ..................................................... 623/17.11

(58) Field of Classification Search
USPC .......... 623/17.11, 17.14, 17.15, 17.16, 20.14, 623/20.22, 20.24; 606/246–249
See application file for complete search history.

(56) References Cited

U.S. PATENT DOCUMENTS

| 3,278,107 A | 10/1966 | Rygg |
| 3,486,505 A | 12/1969 | Morrison |
| 3,872,519 A | 3/1975 | Giannestras et al. |
| 4,021,864 A | 5/1977 | Waugh |
| 4,105,407 A | 8/1978 | Sanderson |
| 4,457,484 A | 7/1984 | Hameister |

(Continued)

FOREIGN PATENT DOCUMENTS

| EP | 1224916 A2 | 7/2002 |
| FR | 2 718 635 A1 | 10/1995 |

(Continued)

OTHER PUBLICATIONS

Medtronic: "Cornerstone-SR Cervical Carbon Cage System", Announcement Medtronic, Jan. 1, 1998, pp. 1-11, XP007916830.

*Primary Examiner* — Pedro Philogene
*Assistant Examiner* — David Comstock
(74) *Attorney, Agent, or Firm* — Lerner, David, Littenberg, Krumholz & Mentlik, LLP

(57) ABSTRACT

This invention improves upon prior art total disc replacements (TDRs) by more closely replicating the kinematics of a natural disc. The preferred embodiments feature two or more fixed centers of rotation (CORs) and an optional variable COR (VCOR) as the artificial disk replacement (ADR) translates from a fixed posterior COR that lies posterior to the COR of the TDR to facilitate normal disc motion. The use of two or more CORs allows more flexion and more extension than permitted by the facet joints and the artificial facet (AF). AF joint-like components may also be incorporated into the design to restrict excessive translation, rotation, and/or lateral bending.

30 Claims, 9 Drawing Sheets

(56) References Cited

U.S. PATENT DOCUMENTS

| | | |
|---|---|---|
| 4,528,980 A | 7/1985 | Kenna |
| 4,759,766 A | 7/1988 | Buettner-Janz et al. |
| 4,759,769 A | 7/1988 | Hedman et al. |
| 4,874,314 A | 10/1989 | Fleer et al. |
| 4,917,704 A | 4/1990 | Frey et al. |
| 4,955,908 A | 9/1990 | Frey et al. |
| 4,997,432 A | 3/1991 | Keller |
| 5,002,576 A | 3/1991 | Fuhrmann et al. |
| 5,030,219 A | 7/1991 | Matsen, III et al. |
| 5,122,130 A | 6/1992 | Keller |
| 5,236,460 A | 8/1993 | Barber |
| 5,258,031 A | 11/1993 | Salib et al. |
| 5,314,477 A | 5/1994 | Marnay |
| 5,370,697 A | 12/1994 | Baumgartner |
| 5,401,269 A | 3/1995 | Buttner-Janz et al. |
| 5,405,400 A | 4/1995 | Linscheid et al. |
| 5,425,773 A | 6/1995 | Boyd et al. |
| 5,458,641 A | 10/1995 | Ramirez Jimenez |
| 5,507,816 A | 4/1996 | Bullivant |
| 5,514,180 A | 5/1996 | Heggeness et al. |
| 5,522,900 A | 6/1996 | Hollister |
| 5,534,029 A | 7/1996 | Shima |
| 5,549,690 A | 8/1996 | Hollister et al. |
| 5,556,431 A | 9/1996 | Buttner-Janz |
| 5,556,432 A | 9/1996 | Kubein-Meesenburg et al. |
| 5,562,738 A | 10/1996 | Boyd et al. |
| 5,599,279 A | 2/1997 | Slotman et al. |
| 5,653,762 A | 8/1997 | Pisharodi |
| 5,674,296 A | 10/1997 | Bryan et al. |
| 5,676,701 A | 10/1997 | Yuan et al. |
| 5,683,464 A | 11/1997 | Wagner et al. |
| 5,683,465 A | 11/1997 | Shinn et al. |
| 5,720,751 A | 2/1998 | Jackson |
| 5,733,290 A | 3/1998 | McCue et al. |
| 5,755,796 A | 5/1998 | Ibo et al. |
| 5,769,856 A | 6/1998 | Dong et al. |
| 5,782,830 A | 7/1998 | Farris |
| 5,782,832 A | 7/1998 | Larsen et al. |
| 5,865,846 A | 2/1999 | Bryan et al. |
| 5,888,223 A | 3/1999 | Bray, Jr. |
| 5,888,226 A | 3/1999 | Rogozinski |
| 5,895,428 A | 4/1999 | Berry |
| 5,899,941 A | 5/1999 | Nishijima et al. |
| 5,916,267 A | 6/1999 | Tienboon |
| 5,928,284 A | 7/1999 | Mehdizadeh |
| 5,989,291 A | 11/1999 | Ralph et al. |
| 6,019,792 A | 2/2000 | Cauthen |
| 6,039,763 A | 3/2000 | Shelokov |
| 6,051,751 A | 4/2000 | Sioshansi et al. |
| 6,063,121 A | 5/2000 | Xavier et al. |
| 6,066,174 A | 5/2000 | Farris |
| 6,066,175 A | 5/2000 | Henderson et al. |
| 6,093,205 A | 7/2000 | McLeod et al. |
| 6,093,207 A | 7/2000 | Pisharodi |
| 6,096,080 A | 8/2000 | Nicholson et al. |
| 6,106,557 A | 8/2000 | Robioneck et al. |
| 6,113,602 A | 9/2000 | Sand |
| 6,113,638 A | 9/2000 | Williams et al. |
| 6,139,550 A | 10/2000 | Michelson |
| 6,143,012 A | 11/2000 | Gausepohl |
| 6,146,421 A | 11/2000 | Gordon et al. |
| 6,156,067 A | 12/2000 | Bryan et al. |
| 6,159,215 A | 12/2000 | Urbahns et al. |
| 6,174,311 B1 | 1/2001 | Branch et al. |
| 6,179,873 B1 | 1/2001 | Zientek |
| 6,179,874 B1 | 1/2001 | Cauthen |
| 6,190,413 B1 | 2/2001 | Sutcliffe |
| 6,193,757 B1 | 2/2001 | Foley et al. |
| 6,213,055 B1 | 4/2001 | Willinger et al. |
| 6,214,005 B1 | 4/2001 | Benzel et al. |
| 6,217,615 B1 | 4/2001 | Sioshansi et al. |
| 6,224,607 B1 | 5/2001 | Michelson |
| 6,228,118 B1 | 5/2001 | Gordon |
| 6,235,034 B1 | 5/2001 | Bray |
| 6,235,060 B1 | 5/2001 | Kubein-Meesenburg et al. |
| 6,241,769 B1 | 6/2001 | Nicholson et al. |
| 6,277,149 B1 | 8/2001 | Boyle et al. |
| 6,296,647 B1 | 10/2001 | Robioneck et al. |
| 6,319,257 B1 | 11/2001 | Carignan et al. |
| 6,325,828 B1 | 12/2001 | Dennis et al. |
| 6,342,057 B1 | 1/2002 | Brace et al. |
| 6,368,350 B1 | 4/2002 | Erickson et al. |
| 6,395,030 B1 | 5/2002 | Songer et al. |
| 6,395,032 B1 | 5/2002 | Gauchet |
| 6,398,815 B1 | 6/2002 | Pope et al. |
| 6,413,259 B1 | 7/2002 | Lyons et al. |
| 6,416,551 B1 | 7/2002 | Keller |
| 6,428,544 B1 | 8/2002 | Ralph et al. |
| 6,432,106 B1 | 8/2002 | Fraser |
| 6,436,102 B1 | 8/2002 | Ralph et al. |
| 6,440,168 B1 | 8/2002 | Cauthen |
| 6,461,359 B1 | 10/2002 | Tribus et al. |
| 6,468,310 B1 | 10/2002 | Ralph et al. |
| 6,471,725 B1 | 10/2002 | Ralph et al. |
| 6,478,796 B2 | 11/2002 | Zucherman et al. |
| 6,478,800 B1 | 11/2002 | Fraser et al. |
| 6,517,580 B1 | 2/2003 | Ramadan et al. |
| 6,524,312 B2 | 2/2003 | Landry et al. |
| 6,527,320 B1 | 3/2003 | Gregg |
| 6,527,804 B1 | 3/2003 | Gauchet et al. |
| 6,540,785 B1 | 4/2003 | Gill et al. |
| 6,562,073 B2 | 5/2003 | Foley |
| 6,576,017 B2 | 6/2003 | Foley et al. |
| 6,579,290 B1 | 6/2003 | Hardcastle et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,582,468 B1 | 6/2003 | Gauchet |
| 6,589,247 B2 | 7/2003 | McGahan et al. |
| 6,602,292 B2 | 8/2003 | Burkinshaw |
| 6,610,093 B1 | 8/2003 | Pisharodi |
| 6,645,248 B2 | 11/2003 | Casutt |
| 6,652,525 B1 | 11/2003 | Assaker et al. |
| 6,652,533 B2 | 11/2003 | O'Neil |
| 6,666,866 B2 | 12/2003 | Martz et al. |
| 6,679,887 B2 | 1/2004 | Nicholson et al. |
| 6,679,915 B1 | 1/2004 | Cauthen |
| 6,682,562 B2 | 1/2004 | Viart et al. |
| 6,706,068 B2 | 3/2004 | Ferree |
| 6,716,245 B2 | 4/2004 | Pasquet et al. |
| 6,740,118 B2 | 5/2004 | Eisermann et al. |
| 6,743,257 B2 | 6/2004 | Castro |
| 6,793,678 B2 | 9/2004 | Hawkins |
| 6,800,093 B2 | 10/2004 | Nicholson et al. |
| 6,835,206 B2 | 12/2004 | Jackson |
| 6,837,905 B1 | 1/2005 | Lieberman |
| 6,896,676 B2 | 5/2005 | Zubok et al. |
| 6,908,484 B2 | 6/2005 | Zubok et al. |
| 6,936,071 B1 | 8/2005 | Marnay et al. |
| 6,972,037 B2 | 12/2005 | Zubok et al. |
| 6,972,038 B2 | 12/2005 | Zubok et al. |
| 6,981,990 B2 | 1/2006 | Keller |
| 6,986,789 B2 | 1/2006 | Schultz et al. |
| 6,991,654 B2 | 1/2006 | Foley |
| 6,994,727 B2 | 2/2006 | Khandkar et al. |
| 6,994,728 B2 | 2/2006 | Zubok et al. |
| 6,994,729 B2 | 2/2006 | Zubok et al. |
| 6,997,954 B2 | 2/2006 | Zubok et al. |
| 6,997,955 B2 | 2/2006 | Zubok et al. |
| 7,022,139 B2 | 4/2006 | Errico et al. |
| 7,056,344 B2 | 6/2006 | Huppert et al. |
| 7,063,725 B2 | 6/2006 | Foley |
| 7,125,425 B2 | 10/2006 | Foley et al. |
| 7,198,643 B2 | 4/2007 | Zubok et al. |
| 7,204,852 B2 | 4/2007 | Marnay et al. |
| 7,226,452 B2 | 6/2007 | Zubok et al. |
| 7,235,104 B2 | 6/2007 | Grinberg et al. |
| 7,270,679 B2 | 9/2007 | Istephanous et al. |
| 7,300,441 B2 | 11/2007 | Haid et al. |
| 7,320,689 B2 | 1/2008 | Keller |
| 7,537,614 B2 | 5/2009 | Baumgartner et al. |
| 7,637,911 B2 | 12/2009 | Zubok et al. |
| 7,794,465 B2 | 9/2010 | Marik et al. |
| 8,277,507 B2 | 10/2012 | Ferree et al. |

(56) References Cited

U.S. PATENT DOCUMENTS

| | | |
|---|---|---|
| 2001/0005796 A1 | 6/2001 | Zdeblick et al. |
| 2001/0007073 A1 | 7/2001 | Zucherman et al. |
| 2001/0010001 A1 | 7/2001 | Michelson |
| 2001/0012938 A1 | 8/2001 | Zucherman et al. |
| 2001/0020170 A1 | 9/2001 | Zucherman et al. |
| 2001/0027343 A1 | 10/2001 | Keller |
| 2002/0004683 A1 | 1/2002 | Michelson |
| 2002/0010511 A1 | 1/2002 | Michelson |
| 2002/0016595 A1 | 2/2002 | Michelson |
| 2002/0017789 A1 | 2/2002 | Holmes et al. |
| 2002/0035400 A1 | 3/2002 | Bryan et al. |
| 2002/0082597 A1 | 6/2002 | Fraser |
| 2002/0082701 A1 | 6/2002 | Zdeblick et al. |
| 2002/0099376 A1 | 7/2002 | Michelson |
| 2002/0107571 A1 | 8/2002 | Foley |
| 2002/0107572 A1 | 8/2002 | Foley et al. |
| 2002/0123750 A1 | 9/2002 | Eisermann et al. |
| 2002/0128712 A1 | 9/2002 | Michelson |
| 2002/0128715 A1 | 9/2002 | Bryan et al. |
| 2002/0143399 A1 | 10/2002 | Sutcliffe |
| 2002/0147450 A1 | 10/2002 | LeHuec et al. |
| 2002/0165612 A1 | 11/2002 | Gerber et al. |
| 2002/0169508 A1 | 11/2002 | Songer et al. |
| 2002/0193880 A1 | 12/2002 | Fraser |
| 2003/0028197 A1 | 2/2003 | Hanson et al. |
| 2003/0028249 A1 | 2/2003 | Baccelli et al. |
| 2003/0040796 A1 | 2/2003 | Ferree |
| 2003/0045939 A1 | 3/2003 | Casutt |
| 2003/0060886 A1 | 3/2003 | Van Hoeck et al. |
| 2003/0069586 A1 | 4/2003 | Errico et al. |
| 2003/0074064 A1 | 4/2003 | Gerbec et al. |
| 2003/0078590 A1 | 4/2003 | Errico et al. |
| 2003/0078668 A1 | 4/2003 | Michelson |
| 2003/0093153 A1 | 5/2003 | Banick et al. |
| 2003/0100949 A1 | 5/2003 | Michelson |
| 2003/0109928 A1 | 6/2003 | Pasquet et al. |
| 2003/0120344 A1 | 6/2003 | Michelson |
| 2003/0125748 A1 | 7/2003 | Li et al. |
| 2003/0135278 A1 | 7/2003 | Eckman |
| 2003/0135279 A1 | 7/2003 | Michelson |
| 2003/0149482 A1 | 8/2003 | Michelson |
| 2003/0167091 A1 | 9/2003 | Scharf |
| 2003/0167092 A1 | 9/2003 | Foley |
| 2003/0176921 A1 | 9/2003 | Lawson |
| 2003/0176922 A1 | 9/2003 | Lawson et al. |
| 2003/0176923 A1 | 9/2003 | Keller et al. |
| 2003/0181982 A1 | 9/2003 | Kuslich |
| 2003/0187454 A1 | 10/2003 | Gill et al. |
| 2003/0191534 A1 | 10/2003 | Viart et al. |
| 2003/0195632 A1 | 10/2003 | Foley et al. |
| 2003/0199981 A1 | 10/2003 | Ferree |
| 2003/0199983 A1 | 10/2003 | Michelson |
| 2003/0204260 A1 | 10/2003 | Ferree |
| 2003/0208273 A1 | 11/2003 | Eisermann et al. |
| 2003/0208274 A1 | 11/2003 | Davis |
| 2003/0216744 A1 | 11/2003 | Longhini et al. |
| 2003/0216810 A1 | 11/2003 | Ralph et al. |
| 2003/0229358 A1 | 12/2003 | Errico et al. |
| 2003/0229397 A1 | 12/2003 | Davis |
| 2003/0233097 A1 | 12/2003 | Ferree |
| 2003/0233146 A1 | 12/2003 | Grinberg et al. |
| 2003/0233148 A1 | 12/2003 | Ferree |
| 2004/0002759 A1 | 1/2004 | Ferree |
| 2004/0002762 A1 | 1/2004 | Hawkins |
| 2004/0010254 A1 | 1/2004 | Cook et al. |
| 2004/0010316 A1 | 1/2004 | William et al. |
| 2004/0024459 A1 | 2/2004 | Ferree |
| 2004/0024461 A1 | 2/2004 | Ferree |
| 2004/0024462 A1 | 2/2004 | Ferree et al. |
| 2004/0030389 A1 | 2/2004 | Ferree |
| 2004/0030390 A1 | 2/2004 | Ferree |
| 2004/0030391 A1 | 2/2004 | Ferree |
| 2004/0034426 A1 | 2/2004 | Errico et al. |
| 2004/0039387 A1 | 2/2004 | Gause et al. |
| 2004/0068318 A1 | 4/2004 | Coates et al. |
| 2004/0068320 A1 | 4/2004 | Robie et al. |
| 2004/0073311 A1 | 4/2004 | Ferree |
| 2004/0117022 A1 | 6/2004 | Marnay et al. |
| 2004/0133281 A1 | 7/2004 | Khandkar et al. |
| 2004/0138750 A1 | 7/2004 | Mitchell |
| 2004/0143270 A1 | 7/2004 | Zucherman et al. |
| 2004/0143332 A1 | 7/2004 | Krueger et al. |
| 2004/0148028 A1 | 7/2004 | Ferree et al. |
| 2004/0167628 A1 | 8/2004 | Foley |
| 2004/0176772 A1 | 9/2004 | Zubok et al. |
| 2004/0176773 A1 | 9/2004 | Zubok et al. |
| 2004/0176774 A1 | 9/2004 | Zubok et al. |
| 2004/0176777 A1 | 9/2004 | Zubok et al. |
| 2004/0176778 A1 | 9/2004 | Zubok et al. |
| 2004/0176843 A1 | 9/2004 | Zubok et al. |
| 2004/0176852 A1 | 9/2004 | Zubok et al. |
| 2004/0193272 A1 | 9/2004 | Zubok et al. |
| 2004/0215198 A1 | 10/2004 | Marnay et al. |
| 2004/0220567 A1 | 11/2004 | Eisermann et al. |
| 2004/0243240 A1 | 12/2004 | Beaurain et al. |
| 2004/0267369 A1 | 12/2004 | Lyons et al. |
| 2005/0021042 A1 | 1/2005 | Marnay et al. |
| 2005/0033430 A1 | 2/2005 | Powers et al. |
| 2005/0043800 A1 | 2/2005 | Paul et al. |
| 2005/0043803 A1 | 2/2005 | Schultz et al. |
| 2005/0055029 A1 | 3/2005 | Marik et al. |
| 2005/0071013 A1 | 3/2005 | Zubok et al. |
| 2005/0085917 A1 | 4/2005 | Marnay et al. |
| 2005/0143749 A1 | 6/2005 | Zalenski et al. |
| 2005/0159819 A1 | 7/2005 | McCormack et al. |
| 2005/0165487 A1 | 7/2005 | Muhanna et al. |
| 2005/0197705 A1 | 9/2005 | Arnin et al. |
| 2005/0228497 A1 | 10/2005 | Ferree et al. |
| 2005/0228500 A1 | 10/2005 | Kim et al. |
| 2005/0240270 A1 | 10/2005 | Zubok et al. |
| 2005/0240271 A1 | 10/2005 | Zubok et al. |
| 2005/0240272 A1 | 10/2005 | Zubok et al. |
| 2005/0240273 A1 | 10/2005 | Khandkar et al. |
| 2005/0256577 A1 | 11/2005 | Baumgartner et al. |
| 2005/0267581 A1 | 12/2005 | Marnay et al. |
| 2005/0267582 A1 | 12/2005 | Ferree et al. |
| 2005/0283237 A1 | 12/2005 | Zucherman et al. |
| 2006/0004377 A1 | 1/2006 | Keller |
| 2006/0030857 A1 | 2/2006 | de Villiers et al. |
| 2006/0036326 A1 | 2/2006 | Baumgartner et al. |
| 2006/0069439 A1 | 3/2006 | Zucherman et al. |
| 2006/0085077 A1 | 4/2006 | Cook et al. |
| 2006/0116768 A1 | 6/2006 | Krueger et al. |
| 2006/0149273 A1 | 7/2006 | Ross et al. |
| 2006/0167461 A1 | 7/2006 | Hawkins et al. |
| 2006/0178748 A1 | 8/2006 | Dinger et al. |
| 2006/0217731 A1 | 9/2006 | Gil et al. |
| 2006/0282020 A1 | 12/2006 | Bertagnoli et al. |
| 2007/0073403 A1 | 3/2007 | Lombardo et al. |
| 2007/0073405 A1 | 3/2007 | Verhulst et al. |
| 2007/0106388 A1 | 5/2007 | Michelson |
| 2007/0112429 A1 | 5/2007 | Muhanna et al. |
| 2007/0118224 A1 | 5/2007 | Shah et al. |
| 2007/0225813 A1 | 9/2007 | Haines |
| 2007/0265707 A1 | 11/2007 | Marnay et al. |
| 2007/0282448 A1 | 12/2007 | Abdou |
| 2008/0027548 A9 | 1/2008 | Ferree et al. |
| 2008/0033563 A1 | 2/2008 | Khandkar et al. |
| 2008/0082169 A1 | 4/2008 | Gittings et al. |
| 2009/0018663 A1 | 1/2009 | Cook et al. |

FOREIGN PATENT DOCUMENTS

| | | |
|---|---|---|
| FR | 2 730 159 A1 | 8/1996 |
| FR | 2 805 985 A1 | 9/2001 |
| FR | 2 824 261 A1 | 11/2002 |
| JP | 06-007390 A | 1/1994 |
| JP | 07241306 A | 9/1995 |
| JP | 08080311 A | 3/1996 |
| JP | 2002528171 A | 9/2002 |
| JP | 2006519673 A | 8/2006 |
| WO | 91/13598 A1 | 9/1991 |
| WO | 94/04100 A1 | 3/1994 |
| WO | 9509587 A1 | 4/1995 |

(56) References Cited

FOREIGN PATENT DOCUMENTS

| | | | |
|---|---|---|---|
| WO | 9710780 | A1 | 3/1997 |
| WO | 9720526 | A1 | 6/1997 |
| WO | 99/11203 | A | 3/1999 |
| WO | 0024342 | A1 | 5/2000 |
| WO | 00 66045 | A1 | 11/2000 |
| WO | 0066011 | A1 | 11/2000 |
| WO | 0101893 | A1 | 1/2001 |
| WO | 0156497 | A2 | 8/2001 |
| WO | 0156513 | A1 | 8/2001 |
| WO | 0195838 | A1 | 12/2001 |
| WO | 0207654 | A2 | 1/2002 |
| WO | 02078514 | A2 | 10/2002 |
| WO | 03053290 | A1 | 7/2003 |
| WO | 03077808 | A2 | 9/2003 |
| WO | 03/084449 | A1 | 10/2003 |
| WO | 03090649 | A1 | 11/2003 |

ARTIFICIAL DISC REPLACEMENTS WITH NATURAL KINEMATICS

CROSS-REFERENCE TO RELATED APPLICATIONS

The present application is a continuation of U.S. patent application Ser. No. 10/512,515, filed on Jun. 3, 2005, which is a national phase entry under 35 U.S.C. §371 of International Application No. PCT/US2003/012500 filed Apr. 23, 2003, published in English, which is a continuation of U.S. patent application Ser. No. 10/420,423 filed Apr. 22, 2003, now U.S. Pat. No. 6,706,068, which claims the benefit of the filing date of U.S. Provisional Patent Application Nos. 60/374,747 filed Apr. 23, 2002, 60/445,958 filed Feb. 7, 2003 and 60/449,642 filed Feb. 24, 2003, the disclosures of which are incorporated herein by reference.

BACKGROUND OF THE INVENTION

This invention relates generally to artificial disc replacements (ADRs) and, more particularly, to ADRs facilitating more natural kinematics.

Many spinal conditions, including degenerative disc disease, can be treated by spinal fusion or through artificial disc replacement (ADR). ADR has several advantages over spinal fusion. The most important advantage of ADR is the preservation of spinal motion. Spinal fusion eliminates motion across the fused segments of the spine. Consequently, the discs adjacent to the fused level are subjected to increased stress. The increased stress increases the changes of future surgery to treat the degeneration of the discs adjacent to the fusion. However, motion through an ADR also allows motion through the facet joints. Motion across arthritic facet joints could lead to pain following ADR. Some surgeons believe patients with degenerative disc and arthritis of the facet joints are not candidates for ADR.

Current ADR designs do not attempt to limit the pressure across the facet joints or facet joint motion. Indeed, prior art ADRs generally do not restrict motion. For example, some ADR designs place bags of hydrogel into the disc space which do not limit motion in any direction. In fact, ADRs of this kind may not, by themselves, provide sufficient distraction across the disc space. ADR designs with metal plates and polyethylene spacers may restrict translation but they do not limit the other motions mentioned above. The articular surface of the poly spacer is generally convex in all directions. Some ADR designs limit motion translation by attaching the ADR halves at a hinge.

One of the most important features of an artificial disc replacement (ADR) is its ability to replicate the kinematics of a natural disc. ADRs that replicate the kinematics of a normal disc are less likely to transfer additional forces above and below the replaced disc. In addition, ADRs with natural kinematics are less likely to stress the facet joints and the annulus fibrosus (AF) at the level of the disc replacement. Replicating the movements of the natural disc also decreases the risk of separation of the ADR from the vertebrae above and below the ADR.

The kinematics of ADRs are governed by the range of motion (ROM), the location of the center of rotation (COR) and the presence (or absence) of a variable center of rotation (VCOR). Generally ROM is limited by the facet joints and the AF. A natural disc has VCOR, that is, the COR varies as the spine bends forward (flexion) and backward (extension). Typically, the vertebra above a natural disc translates forward 1-2 mm as the spine is flexed.

Prior art total disc replacements (TDR), that is, ADRs with rigid plates that attach to the vertebrae, do not replicate the kinematics of the natural disc. Generally, the COR lies too anterior. Most prior art TDRs also rely on a single, fixed COR. As a result, many of the prior art TDRs have a limited ROM.

BRIEF SUMMARY OF THE INVENTION

This invention improves upon prior art TDRs by more closely replicating the kinematics of a natural disc. The preferred embodiments feature two or more fixed centers of rotation (CORs) and an optional variable COR (VCOR) as the ADR translates from a fixed posterior COR to a more anterior COR.

The multiple CORs permit a TDR with a posterior COR that lies posterior to the COR of the TDR to facilitate normal disc motion. The use of two or more CORs allow more flexion and more extension than permitted by the facet joints and the AF. Artificial facet join-like components may also be incorporated into the design to restrict excessive translation, rotation, and/or lateral bending.

DETAILED DESCRIPTION

My U.S. Provisional Patent Application Ser. No. 60/374,747, incorporated herein by reference, describes various improved artificial disc replacements (ADRs), including various embodiments that restrict spinal extension, rotation, translation, and/or lateral bending. In one disclosed configuration, rotation and translocation are limited by a "spoon-on-spoon" type of cooperation. Wedge or trapezoid-shaped ADRs are also presented to preserve lordosis. Fasteners may be used to fix the ADR to upper and lower vertebrae. An optional lip may additionally be provided to prevent the trapping of soft tissue during the movement from a flexion to neutral position.

The present invention extends such teachings through total disc replacements (TDRs) that more closely replicate the kinematics of a natural disc. The preferred embodiments feature two or more fixed centers of rotation (CORs) and an optional variable COR (VCOR) as the ADR translates from a fixed posterior COR to a more anterior COR. The multiple CORs permit a TDR with a posterior COR that lies posterior to the COR of the TDR to facilitate normal disc motion. The use of two or more CORs allow more flexion and more extension than permitted by the facet joints and the AF. Artificial facet joint-like components may also be incorporated into the design to restrict excessive translation, rotation, and/or lateral bending.

Figure 1:
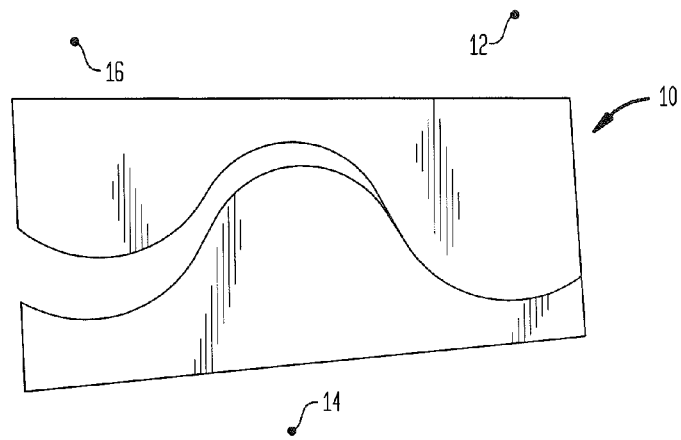
FIG. 1 is a sagittal cross section of a total disc replacement (TDR) according to the invention having three fixed centers of rotation (CORs)
Figure 2:
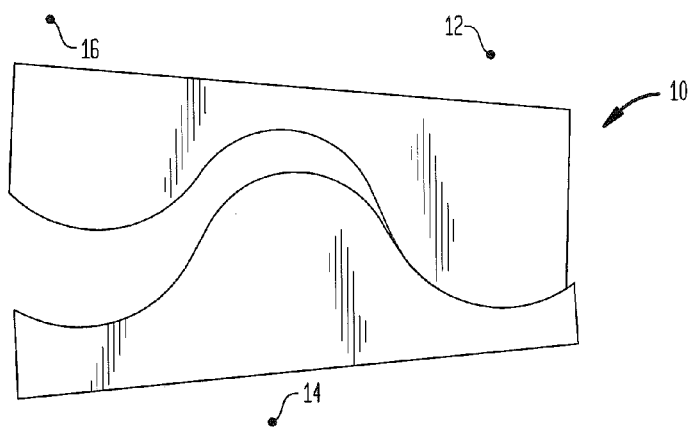
FIG. 2 is a sagittal cross section of the TDR of FIG. 1 extended 5 degrees, more or less.
Figure 3:
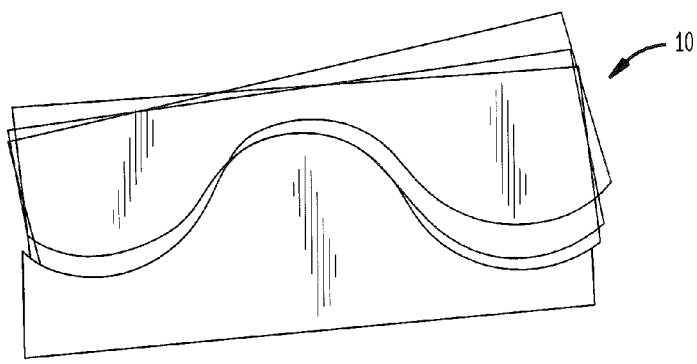
FIG. 3 is a sagittal cross section of the TDR of FIG. 1 showing various degrees of flexion.

FIG. 1 is a sagittal cross section of a TDR 10 according to the invention having three fixed CORs 12, 14, and 16. Articulation occurs at the posterior COR 12 when the spine is in a neutral to extended position. FIG. 2 is a sagittal cross section of the TDR drawn in FIG. 1 with the ADR 10 extended 5 degrees, more or less. FIG. 3 is a sagittal cross section of the TDR drawn in FIG. 1 in various degrees of flexion. As illustrated in the figure, the COR migrates anteriorly from a more posterior COR to a more anterior COR as the TDR is flexed.

Figure 4:
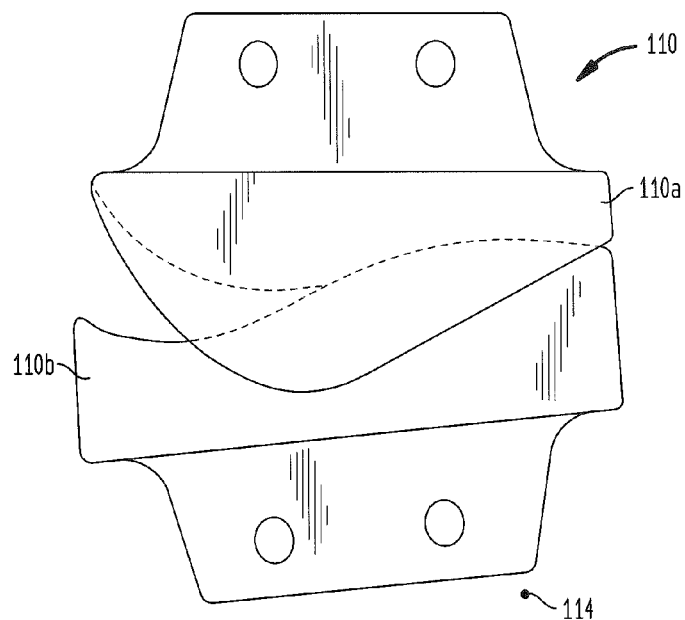
FIG. 4 is a sagittal cross section of another embodiment of a TDR having an anterior COR and a posterior COR.
Figure 5:
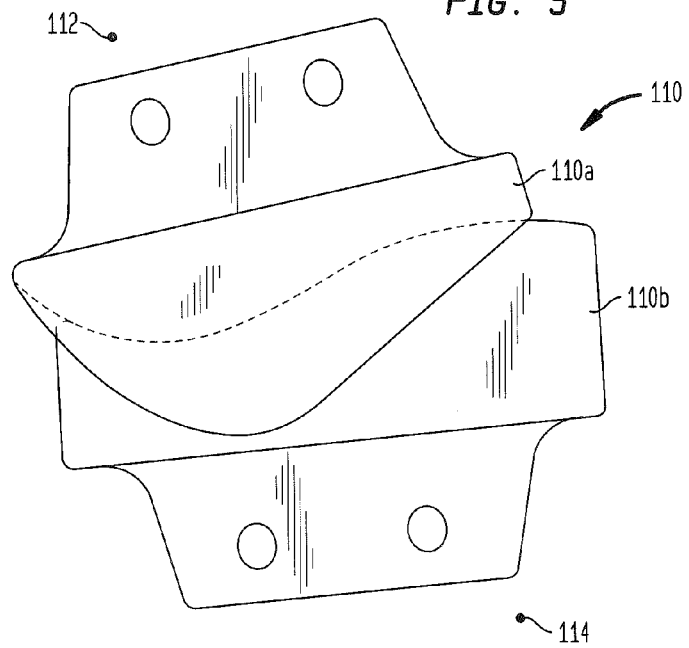
FIG. 5 is a sagittal cross section of the TDR of FIG. 4 in a flexed position.
Figure 6A:
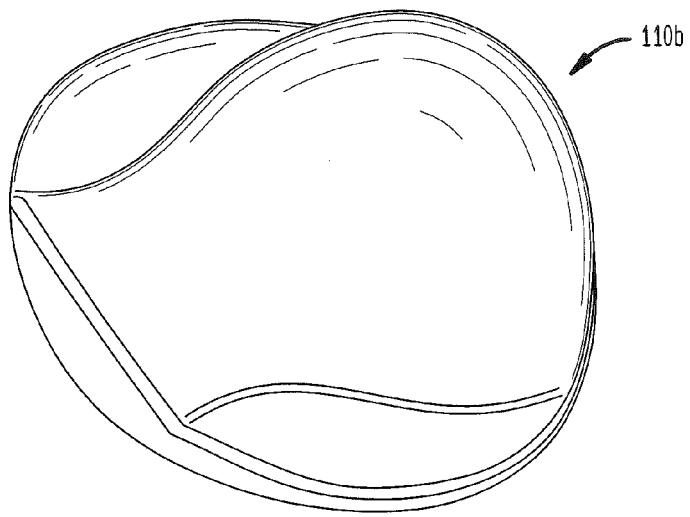
FIGS. 6A and 6B are drawings that show the articulating surfaces of the TDR drawn in FIG. 4.
Figure 6B:
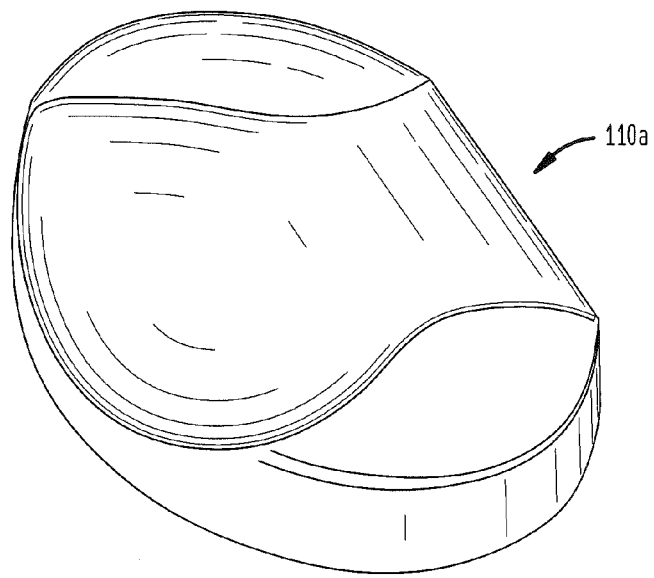

FIG. 4 is sagittal cross section of another embodiment TDR 110 of the invention having an anterior COR 112 and a posterior COR 114. In this case, the TDR 110 articulates at the posterior COR 114 with the TDR in neutral to extended position. FIG. 5 is a sagittal cross section of the TDR 110 drawn in FIG. 4 in a flexed position. Note that the superior TDR endplate 110a translates forward from the posterior COR to the anterior COR as the ADR 110 moves from a neutral or extended position to a flexed position. FIGS. 6A and 6B are a view of the articulating surfaces of the TDR 110 drawn in FIG. 4. The inferior TDR endplate 110b is shown in FIG. 6A, and the inferior surface of the superior TDR endplate 110a is shown in FIG. 6B.

Figure 7:
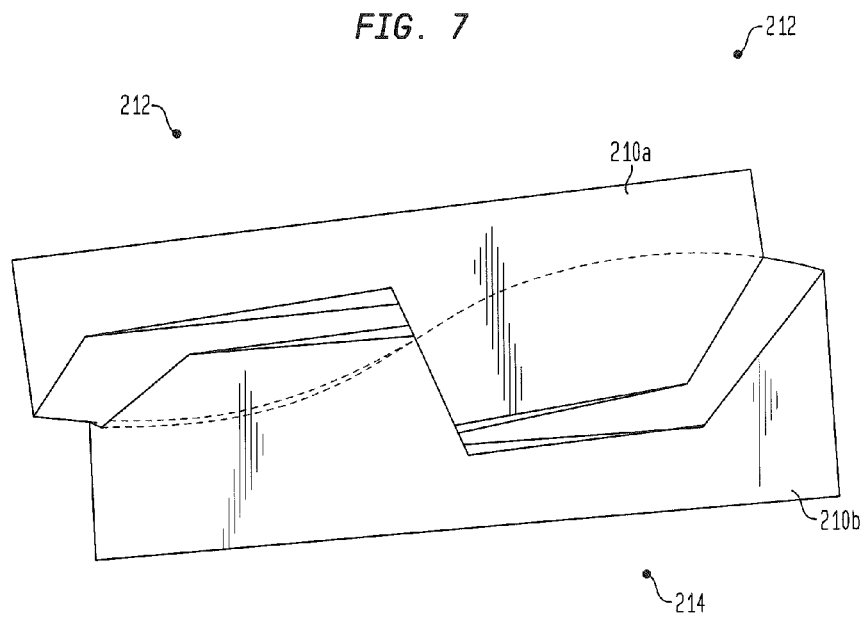
FIG. 7 is a sagittal cross section of another embodiment having an anterior and a posterior COR.
Figure 8:
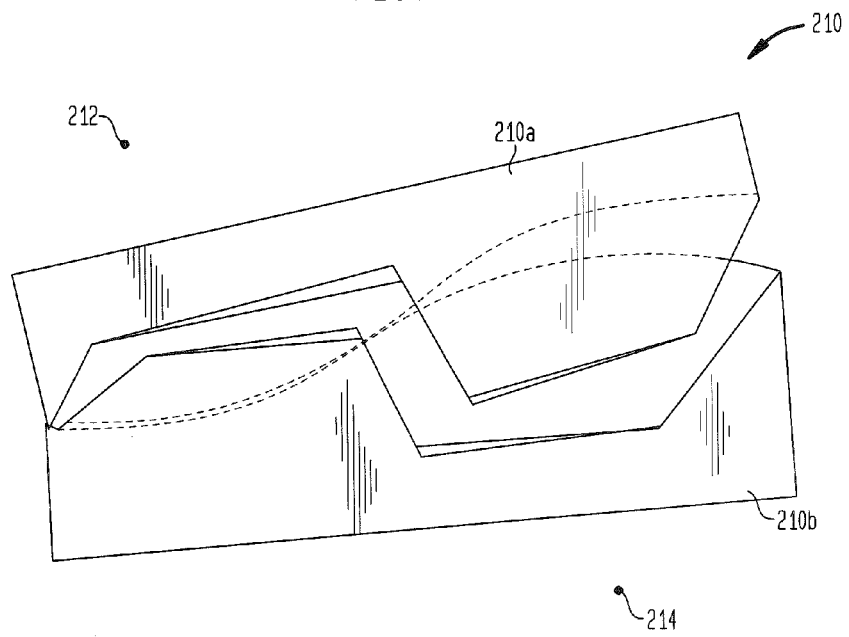
FIG. 8 is a sagittal cross section of the TDR of FIG. 7 in a more flexed position.
Figure 9:
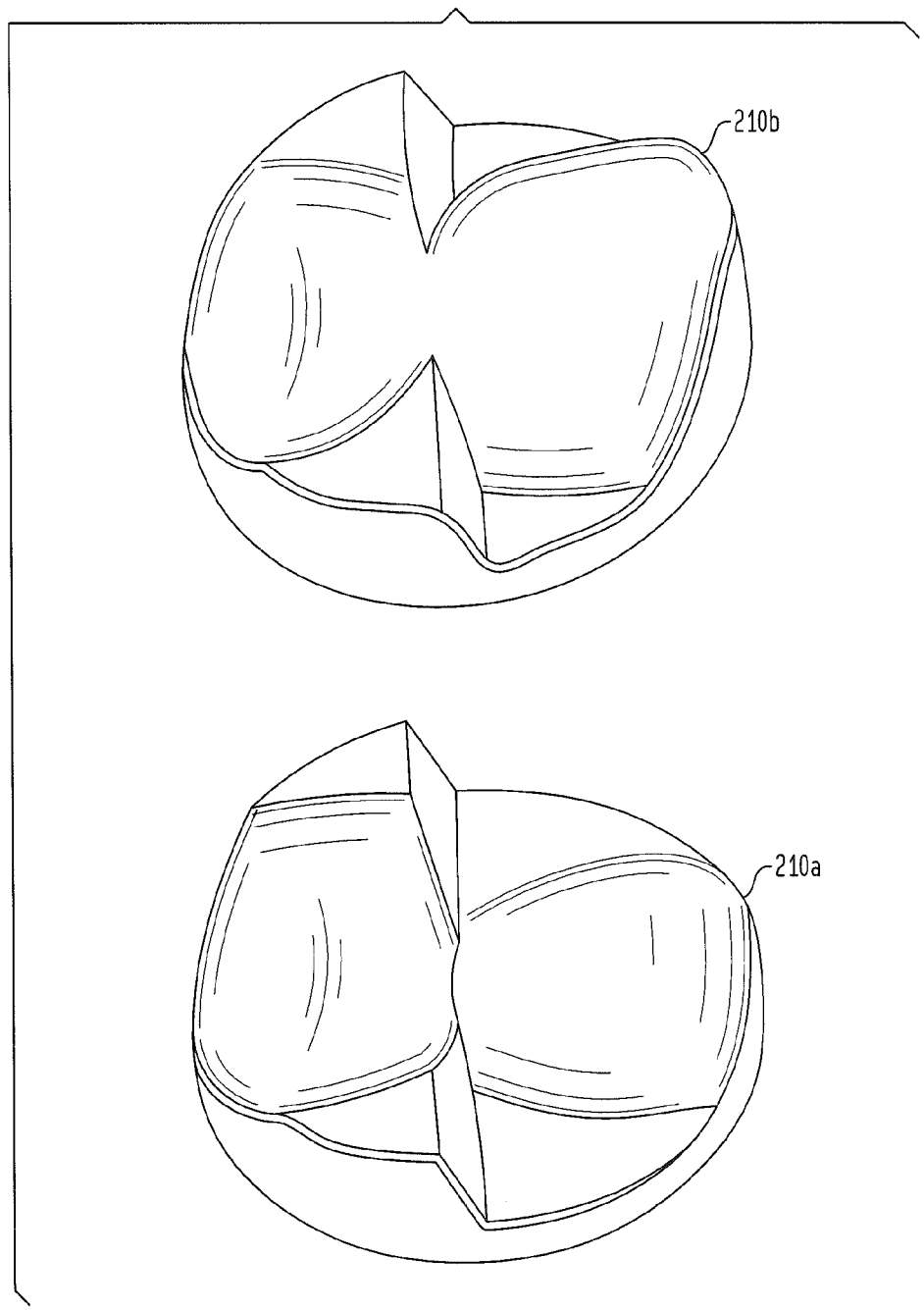
FIG. 9 is a view of the articulating surfaces of the TDR of FIG. 7.
Figure 10:
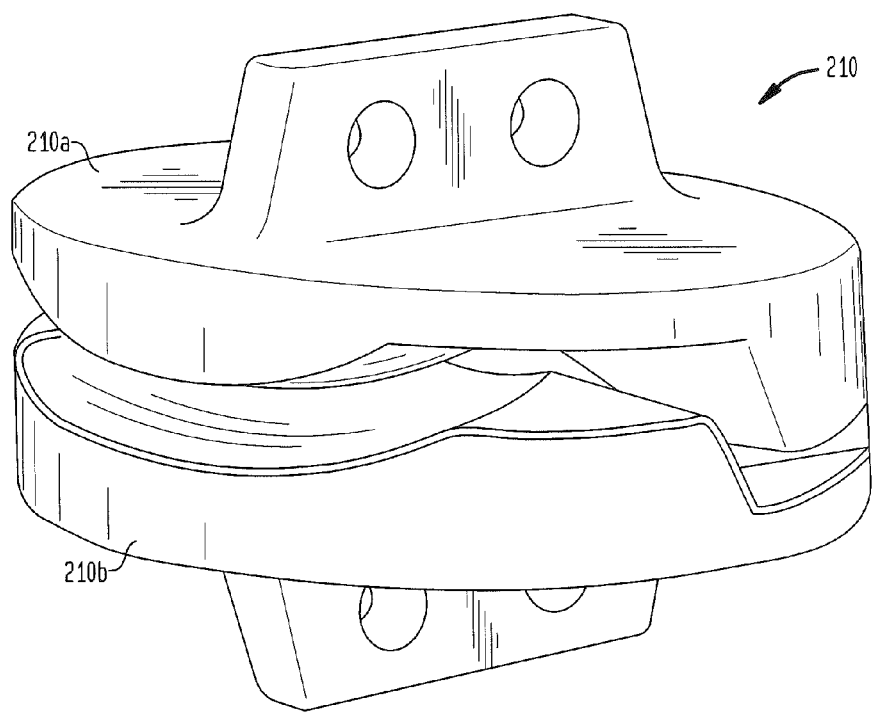
FIG. 10 is an oblique view of the assembled TDR drawn in FIG. 7.

FIG. 7 is a sagittal cross section of a further embodiment of the invention, including an anterior and a posterior COR 212 and 214, respectively. The design also includes novel artificial facet joint-like components that prevent excessive translation, rotation, or lateral bending. FIG. 8 is a sagittal cross section of the TDR 210 drawn in FIG. 7 in a more flexed position. The drawing illustrates a gap between the artificial facet joint-like portions of the device. FIG. 9 is a view of the articulating surfaces of the TDR 210 drawn in FIG. 7. The superior surface of the inferior TDR endplate 210b is drawn on the left. FIG. 10 is an oblique view of the assembled TDR 210 drawn in FIG. 7. This embodiment of the TDR 210 illustrates the use of a toroidal patch and two spherical patches to form the anterior articulating surface of the lower plate. The novel torodial-spherical surface facilitates lateral bending.

Figure 11A:
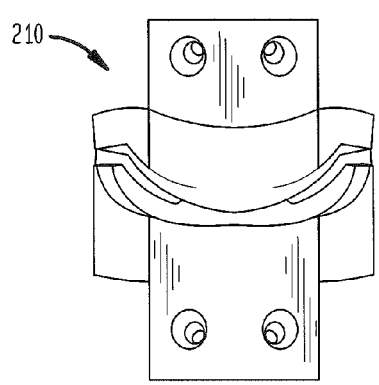
FIG. 11A is a view of the anterior side of a cervical embodiment of the TDR of FIG. 7.
Figure 11B:
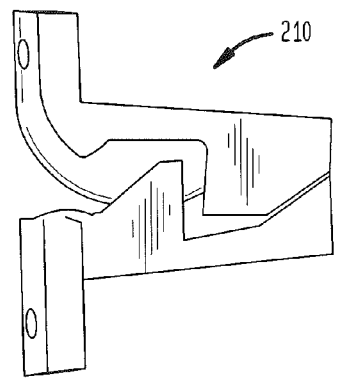
FIG. 11B is a view of the lateral side of the TDR of FIG. 11A.
Figure 11C:
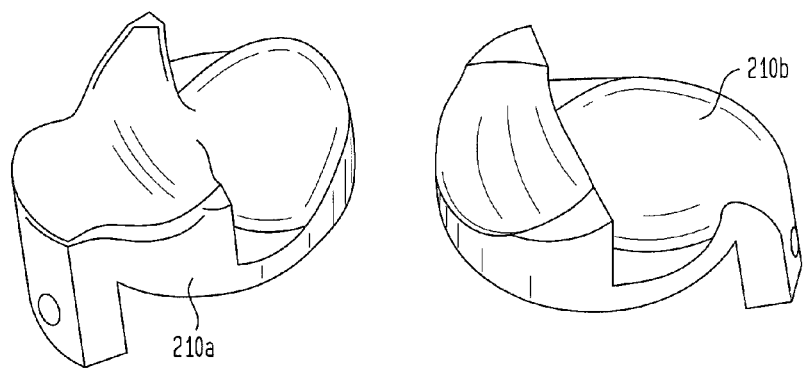
FIG. 11C is a view of the interior of the TDR drawn in FIG. 11A.

FIG. 11A is a view of the anterior side of a cervical embodiment of the TDR 210 drawn in FIG. 7. Screws can be inserted through the holes in the TDR 210 to attach the TDR 210 to the vertebrae. A reversible locking mechanism can be used to prevent the screws from backing out of the vertebrae. FIG. 11B is a view of the lateral side of the TDR 210 drawn in FIG. 11A. FIG. 11C is a view of the anterior of the TDR 210 drawn in FIG. 11A. The superior surface of the inferior component of the TDR is drawn on the left.

Figure 12A:
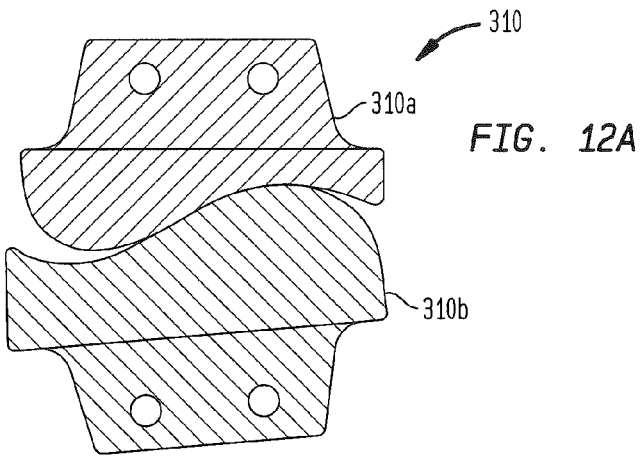
FIG. 12A is a sagittal cross section of yet a further embodiment of an artificial disc replacement according to the invention.

FIG. 12A is a sagittal cross section of another embodiment TDR 310 wherein, in contrast to the embodiment of FIG. 7, the articulating surfaces of the anterior and/or the posterior CORs are not congruent. The use of non-congruent articulating surfaces uncouples translation from rotation. ADRs with non-congruent joint surfaces allow greater spinal flexion and extension without corresponding subluxation of the vertebrae. The spherical projections from the upper and lower ADR endplates 310a and 310b can cooperate to prevent the upper ADR endplate 310a from translating posteriorly over the inferior ADR endplate 310b. The drawing illustrates the different radius of curvature of the components forming the joint in the posterior aspect of the ADR.

Figure 12B:
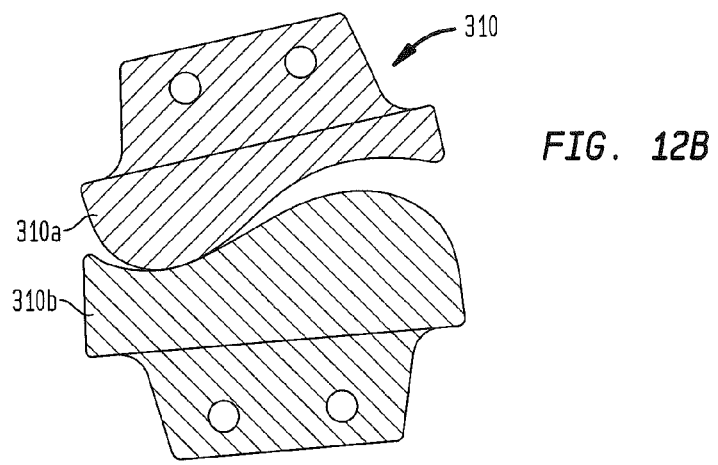
FIG. 12B is a sagittal cross section of the embodiment of the ADR of FIG. 12A.
Figure 12C:
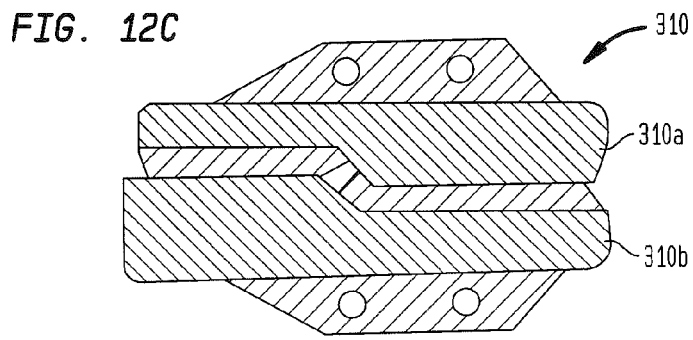
FIG. 12C is a view of the side of the ADR of FIG. 12A.

FIG. 12B is a sagittal cross section of the embodiment of the ADR 310 drawn in FIG. 12A in a flexed position. The drawing illustrates the different radius of curvature of the components forming the joint in the anterior aspect of the ADR 310. FIG. 12C is a view of the side of the ADR 310 drawn in FIG. 12A. Artificial facet joint-like components, similar to those drawn in FIG. 7, prevent excessive forward translation of the upper ADR endplate relative to the lower ADR endplate. The artificial fact joint-like components can also limit axial rotation and lateral bending.

Figure 13A:
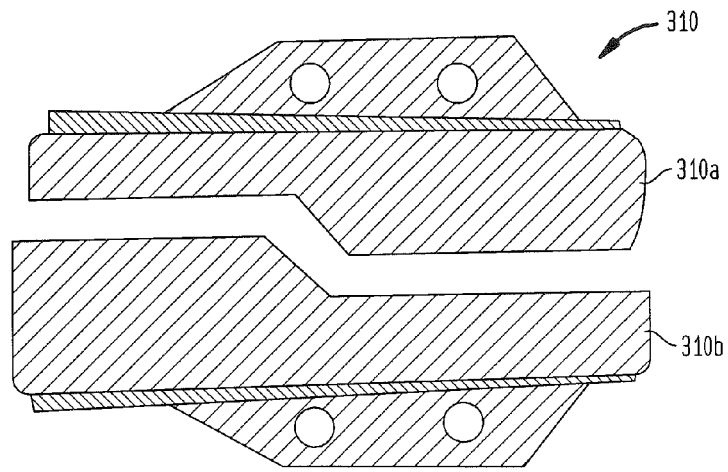
FIG. 13A is a view of the side of the ADR of FIG. 12A including modular shims.
Figure 13B:
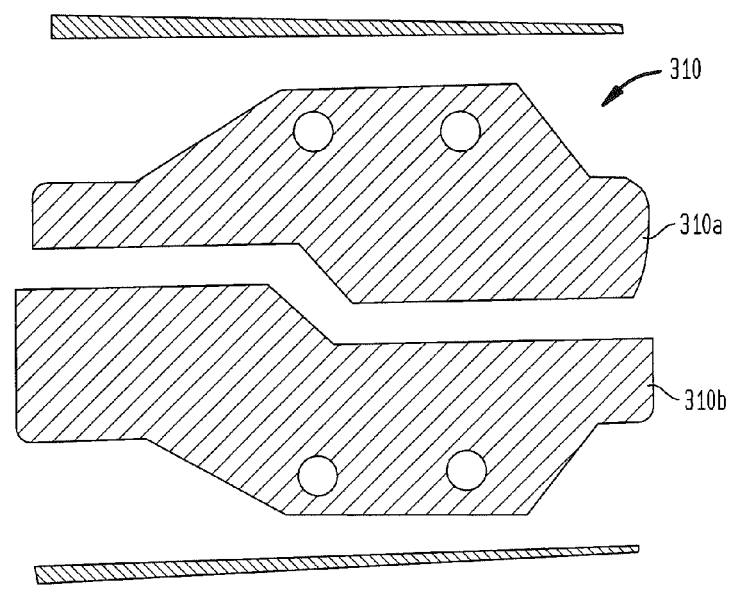
FIG. 13B is an exploded view of the embodiment of the ADR shown in FIG. 13A.

FIG. 13A is a view of the side of the ADR 310 drawn in FIG. 12A, with modular shims. Modular shims can be used to increase lordosis, or wedge shape, of the ADR 310. The modular shims can be attached to the top of the superior ADR endplate 310a and/or the bottom of the inferior ADR endplate 310b. The shims could fasten to the keels of the ADR 310. Alternatively the shims could attach to another part of the ADR endplates 310a and 310b. Lastly, the shims could simply lay on the ADR endplates 310a and 310b. The shim inventory would include shims with different thickness and different angles. FIG. 13B is an exploded view of the embodiment of the ADR drawn in 13 A.

Although surfaces depicted herein are shown as being 'congruent,' this is not necessary according to the invention. For example, a concave surface may have a radius of curvature that is larger than the radius of curvature of an articulating convex surface such that the two surfaces are not in direct or intimate contact at all times. Both symmetrical and asymmetrical joints may also be used. A portion of the back of the posterior joint may be removed to move the posterior COR further posterior and to increase the surface area of the posterior joint by increasing the radius of the surface. The articulating surface may be formed by a toroidal region and a spherical region, in this and other embodiments non-spherical surfaces may also be used to permit translation, rotation or other movements between more controlled articulations. TDRs according to the invention may be used in the cervical, thoracic, or lumbar spine.

ADR/TDRs according to the invention may also be composed of various materials. For example, the components may be constructed of a metal such as chrome cobalt or a ceramic such as aluminum oxide. The novel TDR can also be made of a metal or ceramic coated with a harder or softer second material. That is, one or both of the components may be a metal coated with a ceramic, or a metal or ceramic coated with a diamond-like material or other hardened surface. Alternatively, one or both of the components may be coated with a polymeric (i.e., polyethylene) surface or liner.

The invention claimed is:

1. An artificial disc replacement (ADR) configured for positioning between vertebral bodies having an anterior portion and a posterior portion, comprising:

a superior component with a lower articulating surface; and an inferior component with an upper articulating surface that cooperates with the lower surface through at least one fixed and at least one variable center of rotation (COR), the fixed COR being located in the anterior portion and remaining fixed during movement of the superior component relative to the inferior component, wherein articulation of the superior component relative to the inferior component is defined by a range of motion, and the fixed COR remains fixed through the range of motion.

2. The ADR of claim 1, wherein the lower articulating surface is convex and the upper articulating surface is convex and the upper articulating surface is concave.

3. The ADR of claim 1, wherein the lower and upper articulating surfaces are congruent or non-congruent.

4. The ADR of claim 1, further including at least one set of articulating surfaces forming a separate center of rotation (COR) in the posterior portion.

5. The ADR of claim 4, wherein the anterior and posterior CORs are spherical, symmetrical, or both.

6. The ADR of claim 4, wherein the anterior and posterior CORs are at different vertical heights.

7. The ADR of claim 1, including at least one additional anterior or posterior center of rotation (COR) and substantially smooth transition surface therebetween.

8. The ADR of claim 1, further including one or more facet approximating features that limit excessive translation, rotation and/or lateral bending.

9. An artificial disc replacement (ADR) configured for positioning between vertebral bones, the ADR comprising:

a superior component with a lower articulating surface; and an inferior component with an upper articulating surface that cooperates with the lower surface through two or more centers of rotation (CORs), wherein one of the CORs is a fixed COR that is located between the posterior third and anterior two-thirds of the vertebral bodies, and articulation of the superior component relative to the inferior component is defined by a range of motion, the fixed COR remaining fixed during movement of the superior component relative to the inferior component through the range of motion.

10. The ADR of claim 9, wherein the lower articulating surface is convex and upper articulating surface is convex and the upper articulating surface is concave.

11. The ADR of claim 9, wherein the lower and upper articulating surfaces are congruent or non-congruent.

12. The ADR of claim 9, further including at least one set of articulating surfaces forming a separate center of rotation (COR) in the anterior portion.

13. The ADR of claim 12, wherein the anterior and posterior CORs are spherical, symmetrical, or both.

14. The ADR of claim 9, including at least one additional anterior or posterior center of rotation (COR) and a substantially smooth transition surface therebetween.

15. The ADR of claim 9, further including one or more facet approximating features that limit excessive translation, rotation and/or lateral bending.

16. An artificial disc replacement (ADR) configured for positioning between vertebral bodies having an anterior portion and a posterior portion, comprising:

a superior component with a lower articulating surface; and an inferior component with an upper articulating surface that cooperates with the lower surface through multiple fixed centers of rotation (CORs) and at least one variable center of rotation (COR), the fixed CORs remaining fixed during movement of the superior component relative to the inferior component, wherein articulation of the superior component relative to the inferior component is defined by a range of motion, and the fixed COR remains fixed through the range of motion.

17. The ADR of claim 16, wherein the lower and upper articulating surfaces are congruent or non-congruent.

18. The ADR of claim 16, wherein one of the CORs is located in the anterior portion.

19. The ADR of claim 16, further including at least one set of articulating surfaces forming a separate center of rotation (COR) in the posterior portion.

20. The ADR of claim 19, wherein the anterior and posterior CORs are spherical, symmetrical, or both.

21. The ADR of claim 19, wherein the anterior and posterior CORs are at different vertical heights.

22. The ADR of claim 16, including a substantially smooth transition between the CORs.

23. The ADR of claim 16, further including one or more facet approximating features that limit excessive translation, rotation and/or lateral bending.

24. An artificial disc replacement (ADR) configured for positioning between vertebral bodies, comprising:

a superior component with a lower articulating surface; and an inferior component with an upper articulating surface that cooperates with the lower surface through an anterior-to-posterior-oriented torodial region, the ADR having at least one center of rotation (COR) that is fixed during movement of the superior component relative to the inferior component, wherein articulation of the superior component relative to the inferior component is defined by a range of motion, and the fixed COR remains fixed through the range of motion.

25. The ADR of claim 24, further including at least one spherical articulating region adjacent the torodial region.

26. The ADR of claim 24, including a substantially smooth transition between the torodial region and the spherical region.

27. The ADR of claim 24, wherein the lower and upper articulating surfaces are congruent or non-congruent.

28. The ADR of claim 27, further including at least one set of articulating surfaces forming a separate center of rotation (COR) in the posterior portion.

29. The ADR of claim 28, wherein the anterior and posterior CORs are spherical, symmetrical, or both.

30. The ADR of claim 24, further including one or more facet approximating features that limit excessive translation, rotation and/or lateral bending.

* * * * *